(12) United States Patent
Wang et al.

(10) Patent No.: US 12,403,218 B2
(45) Date of Patent: Sep. 2, 2025

(54) BIOLOGICAL VALVE MATERIAL, PREPARATION METHOD, AND CROSS-LINKING AGENT

(71) Applicant: CHINESE ACADEMY OF MEDICAL SCIENCES INSTITUTE OF BIOMEDICAL ENGINEERING, Tianjin (CN)

(72) Inventors: Zhi-Hong Wang, Tianjin (CN); Jing Liu, Tianjin (CN); Xi-Gang Leng, Tianjin (CN); De-Ling Kong, Tianjin (CN); Yi-Bo Qin, Tianjin (CN)

(73) Assignee: CHINESE ACADEMY OF MEDICAL SCIENCES INSTITUTE OF BIOMEDICAL ENGINEERING, Tianjin (CN)

( * ) Notice: Subject to any disclaimer, the term of this patent is extended or adjusted under 35 U.S.C. 154(b) by 1191 days.

(21) Appl. No.: 16/966,466

(22) PCT Filed: Jun. 24, 2019

(86) PCT No.: PCT/CN2019/092542
§ 371 (c)(1),
(2) Date: Jul. 31, 2020

(87) PCT Pub. No.: WO2019/206343
PCT Pub. Date: Oct. 31, 2019

(65) Prior Publication Data
US 2021/0030923 A1   Feb. 4, 2021

(30) Foreign Application Priority Data

Apr. 24, 2018 (CN) .......................... 201810373023.5

(51) Int. Cl.
*A61L 27/36* (2006.01)
*A61L 27/50* (2006.01)

(52) U.S. Cl.
CPC ....... *A61L 27/3604* (2013.01); *A61L 27/3687* (2013.01); *A61L 27/50* (2013.01); *A61L 2430/20* (2013.01); *A61L 2430/36* (2013.01); *A61L 2430/40* (2013.01)

(58) Field of Classification Search
None
See application file for complete search history.

(56) References Cited

U.S. PATENT DOCUMENTS

2015/0367030 A1* 12/2015 Murray .................. C12P 21/00
                                                                435/68.1
2018/0215875 A1*  8/2018 King ..................... C08G 77/38

FOREIGN PATENT DOCUMENTS

| CN | 1775304   | 5/2006  |
|----|-----------|---------|
| CN | 101690829 | 4/2010  |
| CN | 101721746 | 6/2010  |
| CN | 102114269 | 7/2011  |
| CN | 103191466 | 7/2013  |
| CN | 104623732 | 5/2015  |
| CN | 107744413 | 3/2018  |
| CN | 108498869 | 9/2018  |
| CN | 108578781 | 9/2018  |
| RU | 2430746   | 10/2011 |

OTHER PUBLICATIONS

Shavandi et al. (Biomaterials. Jun. 2018; 167:91-106).*
Finkiel "Sterilization by Gamma Irradiation" (Dec. 2016) Obtained from <https://tuttnauer.com/blog/sterilization-by-gamma-irradiation>.*
Liu et al. (Food Chemistry 133 (2012) 1441-1448).*
Dharunya et al. (2016 Biomed. Mater. 11 045011).*
International Search Report of PCT/CN2019/092542.

* cited by examiner

*Primary Examiner* — Anna R Falkowitz
*Assistant Examiner* — Garen Gotfredson (57) ABSTRACT

The present application discloses a biological valve material which is a swim bladder derived biological valve material. The present application also discloses a method for preparing the biological valve material, includes: decellularizing a raw swim bladder; and cross-linking the decellularized swim bladder with a cross-linking agent. The present application also discloses use of the biological valve material, wherein the biological valve material is used for preparing one or more of a biological heart valve, a biological patch, and an artificial blood vessel. The present application also discloses a cross-linking agent for a bio-based material, including a cross-linking compound and an organic solvent. The cross-linking compound includes a polyphenol compound. The present application also discloses use of the cross-linking agent, wherein the cross-linking agent is used to cross-link the bio-based material after the decellularization treatment.

17 Claims, 8 Drawing Sheets

BIOLOGICAL VALVE MATERIAL, PREPARATION METHOD, AND CROSS-LINKING AGENT

CROSS-REFERENCE TO RELATED APPLICATION

This application claims priority of China Patent Application No. 201810373023.5, entitled "SWIM BLADDER DERIVED BIOLOGICAL VALVE MATERIAL, PREPARATION METHOD AND USE THEREOF", filed on Apr. 24, 2018, in the China National Intellectual Property Administration, the content of which are hereby incorporated by reference in their entirety. This application is a 35 U.S.C. § 371 national application of international patent application No. PCT/CN2019/092542 filed on Jun. 24, 2019, the content of which is also hereby incorporated by reference.

FIELD

The application relates to the technical field of biological valves, and particularly, to a biological valve material, a preparation method thereof, and use thereof, as well as a cross-linking agent and use thereof.

BACKGROUND

In recent years, the worldwide incidence of heart valve diseases continues to rise. In the United States each year, about 80,000 cases of prosthetic heart valve replacement procedures are performed, and about 20,000 people die from the disease directly. The conventional clinical treatment protocols for valvular heart diseases are dominated by mechanical valve replacement and bioprosthetic valve replacement. Patients with mechanical heart valves need a long-term anticoagulation therapy, and the chances of post-operative thrombosis and anticoagulation complications are relatively high.

In the 1960s, biological valves emerged, which do not require the long-term anticoagulation therapy and have excellent hemodynamic performance. In recent years, the use percentage of the biological valves has become higher and higher in valve replacement surgeries. Especially for elderly patients who are at risk of anticoagulation, the biological valves are certainly the best choice for the heart valve replacement surgeries. Meanwhile, transcatheter aortic valve replacement (TAVR) has become a hot new valve treatment technology in the world. The artificial valve used by TAVR is a biological valve, so that the demand for the biological valves will rapidly increase in the future. At present, the clinically used artificial biological valves are mostly derived from bovine pericardia, porcine pericardia, and porcine aortic valves. It is generally believed that the lifetime of the biological valves is about 10-15 years, which cannot meet an expected durability. The most important problem that restricts the lifetime is the serious calcification problem of the biological valves.

SUMMARY

In view of this, the present application discloses an anti-calcification biological valve material, a preparation method and use thereof, and a cross-linking agent and use thereof.

The biological valve material is a swim bladder derived biological valve material.

In an embodiment, the swim bladder derived biological valve material is obtained by decellularizing a swim bladder.

In an embodiment, the swim bladder derived biological valve material is obtained by decellularizing a swim bladder and then cross-linking by using a cross-linking agent. The cross-linking agent includes a cross-linking compound.

In an embodiment, the swim bladder is obtained from a teleost fish.

In an embodiment, the teleost fish includes one or more of a Silver carp, a Grass carp, an Amur carp, a Yellow croaker, a Sturgeon, a Scomberomorus, and a Sciaenidae. It should be noted that, in addition to the fish species listed above, the source of the swim bladder used in the present application can also be selected from other fish species having a swim bladder, which should all fall within the protection scope of the present application.

In an embodiment, the cross-linking compound is at least one of a polyphenol compound and glutaraldehyde.

In an embodiment, the polyphenol compound is selected from one or more of flavonoids, tannins, phenolic acids, and anthocyanins.

In an embodiment, the polyphenol compound is selected from one or more of proanthocyanidins, curcumin, resveratrol, puerarin, aloin, and aloe emodin.

In an embodiment, the cross-linking agent further includes an organic solvent or an aqueous solution, and the cross-linking compound is dissolved in the organic solvent or the aqueous solution. The organic solvent is selected from ethanol and/or dimethyl sulfoxide. The aqueous solution is selected from a PBS solution and/or a D-Hanks solution.

In an embodiment, the cross-linking compound in the cross-linking agent is a polyphenol compound, and a ratio of a mass of the polyphenol compound to a volume of the organic solvent is 1 mg:(0.1 to 1000.0) mL.

In an embodiment, the cross-linking agent further includes a buffer solution, and the buffer solution is an aqueous solution.

In an embodiment, a concentration of the cross-linking compound in the cross-linking agent is 0.001 mg/mL to 10.0 mg/mL.

In an embodiment, the pH value of the cross-linking agent is 5.0 to 9.0.

A method for preparing the biological valve material includes:
 decellularizing a raw swim bladder; and
 cross-linking the decellularized swim bladder with a cross-linking agent.

In an embodiment, the raw swim bladder is a fresh swim bladder preserved in a first buffer solution containing penicillin and streptomycin.

In an embodiment, in the first buffer solution, a concentration of penicillin is 50 U/mL to 150 U/mL, and a concentration of streptomycin is 0.05 mg/mL to 0.5 mg/mL.

In an embodiment, before decellularizing the raw swim bladder, the method further includes a step of rinsing the raw swim bladder multiple times with a sterile second buffer solution.

In an embodiment, the step of decellularizing includes:
 treating the raw swim bladder with a surfactant solution;
 soaking the raw swim bladder after the surfactant treatment in a third buffer solution for 1 day to 20 days; and
 treating the raw swim bladder, after the soaking in the third buffer solution, in a solution containing deoxyribonuclease and ribonuclease.

In an embodiment, the step of treating the raw swim bladder with the surfactant solution includes:

treating the raw swim bladder in an anionic surfactant solution with a mass percentage of 0.05% to 2% at room temperature for 6 hours to 24 hours; and treating the raw swim bladder, after the anionic surfactant treatment, in a non-ionic surfactant solution with a mass percentage of 0.05% to 2% at room temperature for 30 minutes to 120 minutes.

In an embodiment, in the solution containing deoxyribonuclease and ribonuclease, the concentration of deoxyribonuclease is 0.1 mg/mL to 0.3 mg/mL, and the concentration of the ribonuclease is 15 mg/mL to 20 mg/mL.

In an embodiment, before cross-linking the swim bladder, the method further includes irradiating the swim bladder after the decellularization treatment with Co60 for 1 hour to 72 hours.

In an embodiment, the step of cross-linking the decellularized swim bladder with the cross-linking agent includes: immersing the decellularized swim bladder in the cross-linking agent.

In an embodiment, the temperature of the cross-linking is 10° C. to 40° C., and the time of the cross-linking is 10 minutes to 48 hours.

In an embodiment, the method further includes a step of rinsing the cross-linked swim bladder.

Use of the biological valve material is provided, wherein the biological valve material is used for preparing one or more of a biological heart valve, a biological patch, and an artificial blood vessel.

In an embodiment, the biological heart valve includes an interventional valve and/or an implanted valve.

A cross-linking agent for a bio-based material includes a cross-linking compound and an organic solvent, and the cross-linking compound includes a polyphenol compound.

In an embodiment, the polyphenol compound is selected from one or more of flavonoids, tannins, phenolic acids, and anthocyanins.

In an embodiment, the polyphenol compound is selected from one or more of proanthocyanidins, curcumin, resveratrol, puerarin, aloin, and aloe emodin.

Use of the cross-linking agent is provided, wherein the cross-linking agent is used to cross-link the bio-based material after the decellularization treatment.

In an embodiment, the bio-based material is one or more of a porcine pericardium, a bovine pericardium, a small intestine, a swim bladder, and a mesentery.

In an embodiment, in the decellularizion, α-galactosidase is used to remove α-galactoside from the bio-based material.

In an embodiment, a concentration of the α-galactosidase is 0.01 U/mL to 0.5 U/mL.

In an embodiment, the bio-based material is a mammal derived bio-based material.

In an embodiment, the bio-based material is selected from one or more of a porcine pericardium, a bovine pericardium, a small intestine, and a mesentery.

Compared with the traditional bovine pericardial biological valve, both surfaces of the swim bladder derived biological valve material provided by this application are smooth; and the material has uniform thickness, almost no fat and no other adhesion tissues, so that the processing procedure of raw material is simple, and the yield of the swim bladder derived biological valves is relatively high.

The swim bladder derived biological valve material provided by the present application has mechanical properties that are comparable to those of the bovine pericardial material, and far superior anti-calcification performance than that of the bovine pericardial material, avoiding the defect of insufficient lifetime of the bovine pericardial material, solves the problems such as poor durability and easy calcification of the bovine pericardial material.

The cross-linking agent for bio-based materials provided by the present application contains natural polyphenol compounds. After modification of the bio-based materials with the cross-linking agent, the obtained materials have good mechanical properties and stability, can significantly reduce tissue calcification and prolong lifetime.

BRIEF DESCRIPTION OF THE DRAWINGS

In order to clearly explain technical solutions of the present application, the following drawings, which are to be referred in the description of the embodiments, are briefly described below. Obviously, the drawings in the following description only show some embodiments of the present application, and those skilled in the art can obtain other drawings according to the following drawings without any creative work.

DETAILED DESCRIPTION

In order to make the objectives, features and advantages of the present disclosure more comprehensible, the exemplified embodiments of the present disclosure will be illustrated in detail below with reference to the drawings. Many details are described in the following description, in order to understand the present disclosure thoroughly. However, the disclosure can be implemented in many other ways other than the ways described herein. Those skilled in the art can make some similar improvements without departing from the spirit of the present disclosure. Therefore, the present disclosure is not limited to the exemplified embodiments described below.

An embodiment of the present application provides a biological valve material, which is a swim bladder derived biological valve material.

Compared with the traditional bovine pericardial biological valve, the swim bladder derived biological valve material provided by this application has two smooth opposite surfaces, uniform thickness, almost no fat and no other adhesion tissues, so that the processing procedure if raw material is simple, and the yield of the swim bladder derived biological valves is relatively high. In addition, the swim bladder derived biological valve material has mechanical properties that are comparable to those of the bovine pericardial material, and far superior anti-calcification performance than that of the bovine pericardial material, avoids the defect of insufficient lifetime of the bovine pericardial material, solves the problem such as poor durability and easy calcification of the bovine pericardial material.

The swim bladder is a membrane structure mainly composed of collagen fibers and elastic fibers. Both surfaces of the swim bladder are smooth. The swim bladder is a water depth regulator, which is found in most bony fish and can constantly contracting and expanding to adjust the air content thereby changing the position of fish in the water. In an embodiment, the swim bladder is obtained from a teleost fish. The teleost fish can include one or more of a Silver carp, a Grass carp, an Amur carp, a Yellow croaker, a Sturgeon, a Scomberomorus, and a Sciaenidae. It should be noted that, in addition to the fish species listed above, the source of the swim bladder used in the present application can also be selected from other fish species having a swim bladder, which should all fall within the protection scope of the present application.

In an embodiment, the swim bladder derived biological valve material is obtained by decellularizing a swim bladder. By decellularizing, the lipids and nucleic acids of the swim bladder are removed to reduce the immunogenicity of the swim bladder. After the decellularization, the swim bladder retains a natural three-dimensional scaffold structure composed of proteins such as collagen, elastin, fibronectin, and laminin. The scaffold structure is an extracellular matrix and contains many functional proteins such as glycoproteins and proteoglycans, so as to have good biocompatibility.

In an embodiment, the swim bladder derived biological valve material is obtained from cross-linking the decellularized swim bladder by using a cross-linking agent. The decellularized bio-based materials used in the human body, such as artificial heart valves, need to be cross-linked to remove immunogenicity and maintain the original structure and mechanical properties of the material. A biological valve is a valve prosthesis that is processed from an animal or human heart valve or a pericardium that has similar structure and function of the human body. For the biological valves, the clinical success rate of the allogeneic valves is high, but their sources are limited; and although heterospecies valves have a wide range of sources, they have antigenicity and must be cross-linked before they can be used. The cross-linked biological valve has a degree of strength and toughness, basically retains the collagen structure of the biological valve, reduces immunogenicity, and largely avoids the disadvantages of life-long anticoagulation after the artificial heart valve replacement. In addition, the cross-linked decellularized biological valve is not easy to be infected by certain pathogenic bacteria or viral diseases.

The cross-linking agent includes a cross-linking compound and a solvent. The cross-linking compound can be selected from one or more of glutaraldehyde and a polyphenol compound.

Optionally, the cross-linking compound is a polyphenol compound. The polyphenol compound refers to a natural polyphenol compound, which has beneficial functions such as anti-oxidation, strengthening of blood vessel walls, reducing blood fat, preventing arteriosclerosis, and antithrombosis. The toxicity of the polyphenol compound is far lower than glutaraldehyde, and has no carcinogenicity. The polyphenol compound is convenient to obtain, has high yield and low cost. The biological valve treated with the polyphenol compound shows more collagen expressions and depositions, no calcification after transplantation, and mechanical strength and enzymatic resistance comparable to the glutaraldehyde treated biological valves. Compared with the conventional cross-linking agents, the polyphenol compound cross-linked biological valve in the embodiment of the present application has better mechanical properties and stability, can significantly reduce tissue calcification, inflammation and thrombus, and can reduce biological toxicity, thereby prolonging the lifetime, overcome the defects of serious calcification and poor durability of the biological heart valve material treated by the conventional cross-linking method, thereby further improving the anti-calcification performance of the swim bladder derived biological valve material.

In an embodiment, the polyphenol compound can be selected from one or more of flavonoids, tannins, phenolic acids, and anthocyanins.

In an embodiment, the polyphenol compound can be selected from one or more of proanthocyanidins, curcumin, resveratrol, puerarin, aloin and aloe-emodin.

In an embodiment, the cross-linking agent further includes an organic solvent or an aqueous solution, and the cross-linking compound is dissolved in the organic solvent or the aqueous solution. The organic solvent can be selected from ethanol and/or dimethyl sulfoxide. The aqueous solution is selected from a PBS solution and/or a D-Hanks solution.

In an embodiment, the cross-linking compound is a polyphenol compound, and a ratio of a mass of the polyphenol compound to a volume of the organic solvent in the cross-linking agent can be 1 mg:(0.1 to 1000.0) mL.

In an embodiment, the pH value of the cross-linking agent is 5.0 to 9.0.

In an embodiment, the cross-linking compound is glutaraldehyde, and a mass percentage of glutaraldehyde in the cross-linking agent can be 0.5% to 1%.

In an embodiment, the cross-linking agent further includes a buffer solution, and the buffer solution can be an aqueous solution. The aqueous solution can be a phosphate buffered saline (PBS) solution and/or a D-Hanks solution. The buffer solution is used to dilute the cross-linking agent.

In an embodiment, the PBS solution includes: 7 g/L to 9 g/L sodium chloride (NaCl), 1 g/L to 2 g/L disodium hydrogen phosphate ($Na_2HPO_4$), 0.2 g/L to 0.3 g/L potassium dihydrogen phosphate ($KH_2PO_4$), 0.15 g/L to 0.25 g/L potassium chloride (KCl). The D-Hanks solution (simulated body fluid) includes: 7 g/L to 9 g/L sodium chloride (NaCl), 0.087 g/L to 1 g/L disodium hydrogen phosphate heptahydrate ($Na_2HPO_4 \cdot 7H_2O$), 0.3 g/L to 0.5 g/L potassium chloride (KCl), 39 g/L to 41 g/L potassium dihydrogen phosphate ($KH_2PO_4$), 0.25 g/L to 0.45 g/L sodium hydroxide (NaHCO$_3$). Optionally, the formula of the PBS solution (1 L) is as follows: 8 g sodium chloride (NaCl), 1.42 g disodium hydrogen phosphate (Na$_2$HPO$_4$), 0.27 g potassium dihydrogen phosphate (KH$_2$PO$_4$), and 0.2 g potassium chloride (KCl). Optionally, the formula of the D-Hanks solution (simulated body fluid) (1 L) is as follows: 8.0 g sodium chloride (NaCl), 0.09 g disodium hydrogen phosphate heptahydrate (Na$_2$HPO$_4$·7H$_2$O), 0.4 g potassium chloride (KCl), 40.06 g potassium dihydrogen phosphate (KH$_2$PO$_4$), and 0.35 g sodium hydroxide (NaHCO$_3$).

In an embodiment, a concentration of the cross-linking compound in the cross-linking agent can be 0.001 mg/mL to 10.0 mg/mL.

Figure 1:
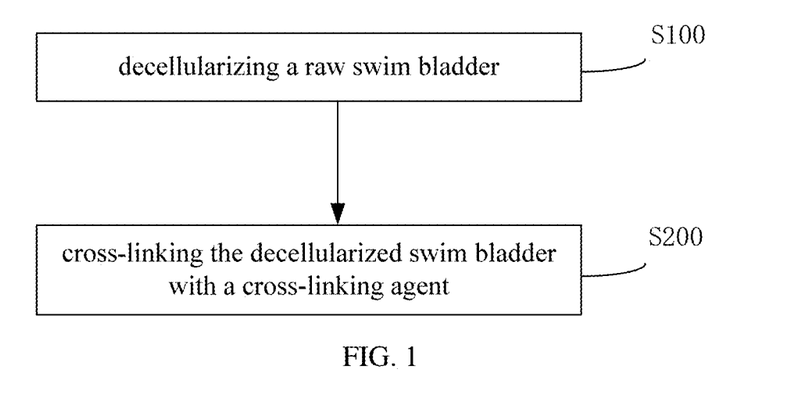
FIG. 1 is a flowchart of a method for preparing a biological valve according to an embodiment of the present application.

An embodiment of the present application further provides a method for preparing the biological valve material, including:
S100, decellularizing a raw swim bladder; and
S200, cross-linking the decellularized swim bladder with a cross-linking agent.

In an embodiment, the raw swim bladder is a fresh swim bladder preserved in a first buffer solution containing penicillin and streptomycin. In an embodiment, the raw swim bladder is a fresh swim bladder preserved in a PBS solution containing penicillin and streptomycin. The fresh swim bladder was taken out from a live fish, and then preserved in a PBS solution containing penicillin and streptomycin, and stored in an ice bag for later use. The first buffer solution can be the aqueous solution, and the aqueous solution can be one or more of the PBS solution and the D-Hanks solution. In the first buffer solution, a concentration of the penicillin can be 50 U/mL to 150 U/mL, and a concentration of the streptomycin can be 0.05 mg/mL to 0.5 mg/mL. In an embodiment, the first buffer solution can be the PBS solution, the concentration of penicillin is 100 U/mL, and the concentration of streptomycin is 0.1 mg/mL.

In an embodiment, before performing the decellularization treatment on the raw swim bladder, the method further includes the step of rinsing the raw swim bladder multiple times with a sterile second buffer solution to remove impurities on the surface of the raw swim bladder. The second buffer solution can be the aqueous solution, and the aqueous solution can be one or more of the PBS solution and the D-Hanks solution.

In an embodiment, the step of decellularizing can include:
S142, treating the raw swim bladder with a surfactant solution;
S144, soaking the raw swim bladder after the surfactant treatment in a third buffer solution for 1 day to 20 days; and
S146, treating the raw swim bladder, after the soaking in the third buffer solution, in a solution containing deoxyribonuclease and ribonuclease.

In an embodiment, the surfactant can include one or more of an anionic surfactant and a non-ionic surfactant. The combination of the anionic surfactant and the non-ionic surfactant is used to remove cells and fat from the raw swim bladder. The third buffer solution can be the aqueous solution, and the aqueous solution can be one or more of the PBS solution and the D-Hanks solution.

The step S142 of the treating the raw swim bladder with the surfactant solution can includes:
treating the raw swim bladder in an anionic surfactant solution with a mass percentage of 0.05% to 2% at room temperature for 6 hours to 24 hours; and
treating the raw swim bladder, after the anionic surfactant treatment, in a non-ionic surfactant solution with a mass percentage of 0.05% to 2% at room temperature for 30 minutes to 120 minutes.

In an embodiment, the anionic surfactant can be, but not limited to, sodium dodecyl sulfonate (SDS), and the mass concentration of the anionic surfactant can be 0.05% to 2%. The non-ionic surfactant can be, but not limited to, Triton X-100, and the mass concentration of the non-ionic surfactant can be 0.05% to 2%. In an embodiment, after the anionic surfactant treatment and before the non-ionic surfactant treatment, the method can include: rinsing the raw swim bladder after the anionic surfactant treatment with the buffer solution, to remove the anionic surfactant and cell debris.

In step S144, the surfactant remaining on the surface of the raw swim bladder is removed by the third buffer solution. The treatment time in the third buffer solution can be 7 days to 14 days. The treatment temperature can be 4° C.

In the step S146, in the solution containing deoxyribonuclease (DNase) and ribonuclease (RNase), a concentration of the deoxyribonuclease can be 0.1 mg/mL to 0.3 mg/mL, and a concentration of the ribonuclease can be 15 mg/mL to 20 mg/mL. The solvent in the solution containing deoxyribonuclease and ribonuclease can be one or more of the PBS solution and the D-Hanks solution. Through the treatment of the deoxyribonuclease and the ribonuclease, the RNA and DNA in the nucleus and the cytoplasm of the raw swim bladder are removed. The treating time can be 6 hours to 24 hours. The step of treating can include shaking, and the rotating speed of the shaking can be 100 rpm to 150 rpm.

In an embodiment, the step of the decellularizing further includes: after the step S146, shaking the swim bladder in the PBS solution and/or the D-Hanks solution for 5 hours to 24 hours, to thoroughly remove cell residues, debris, free proteins, and nucleic acids. The rotating speed can be 100 rpm to 150 rpm.

In an embodiment, the step of decellularizing can include: placing the raw swim bladder in a 1% SDS solution for 6 hours to 24 hours at room temperature; transferring the swim bladder into 1% Triton X-100 for 0 to 120 minutes at room temperature; then immersing and rinsing the swim bladder in the PBS solution for 1-20 days; and then shaking to digest the swim bladder in a solution containing 0.2 mg/mL DNase and 20 mg/mL RNase overnight.

In an embodiment, before the cross-linking treatment of the swim bladder, the method further includes irradiating the swim bladder after the decellularization treatment with Co60 for 1 hour to 72 hours for sterilization. In the Co60 radiation, the fish bladder can be enclosed and sealed.

In step S200, glutaraldehyde or the polyphenol compound can be used as the cross-linking agent. Specifically, the decellularized swim bladder can be immersed in the cross-linking agent.

The cross-linking agent is preferred to be the polyphenol compound. In an embodiment, the cross-linking temperature can be 10° C. to 40° C., and the cross-linking time can be 10 minutes to 48 hours.

In an embodiment, the method for preparing the biological valve further includes: a step of rinsing the swim bladder after the cross-linking. The rinsing solution can be the PBS solution and/or the D-Hanks solution, and the cross-linking agent on the surface of the biological valve can be removed by the rinsing.

An embodiment of the present application further provides an application of the biological valve material, which is used for preparing a biological heart valve and/or a biological patch. The biological heart valve can include an interventional valve and/or an implanted valve.

An embodiment of the present application further provides a cross-linking agent for bio-based materials, including a cross-linking compound and an organic solvent, and the cross-linking compound includes a polyphenol compound.

In an embodiment, the polyphenol compound can be selected from one or more of flavonoids, tannins, phenolic acids, and anthocyanins.

In an embodiment, the polyphenol compound can be selected from one or more of proanthocyanidins, curcumin, resveratrol, puerarin, aloin and aloe emodin.

An embodiment of the present application further provides an application of the cross-linking agent, which is used to cross-link the bio-based material after the decellularization treatment. The bio-based material can be one or more of a porcine pericardium, a bovine pericardium, a small intestine, a swim bladder, and a mesentery.

The method for preparing a biological valve from the bio-based materials other than the swim bladder using the cross-linking agent can be the same as that from the swim bladder, which will not be repeated herein.

In a specific embodiment, the bio-based material is a mammal derived bio-based material, and the step of decellularizing can include: using α-galactosidase to remove α-galactoside from the bio-based material. The inventors have found through a large number of studies and experiments that α-galactoside of heterologous mammals has an important effect on the immunogenicity of implanted biological valves. In an embodiment of this application, α-galactosidase is used to remove α-galactoside in the mammalian bio-based material to reduce the immunogenicity of the biological valve material, and improve the biocompatibility of the biological valve after it is implanted into a human body.

In an embodiment, a concentration of the α-galactosidase can be 0.01 U/mL to 0.5 U/mL. In an embodiment, the bio-based material is selected from one or more of a porcine pericardium, a bovine pericardium, a small intestine, and a mesentery. The polyphenol compounds in the cross-linking agent have the functions such as anti-oxidation, strengthening of blood vessel walls, promoting gastrointestinal digestion, reducing blood fat, increasing immunity, preventing arteriosclerosis, and antithrombosis, and are a group of degradable, non-toxic, non-carcinogenic natural substances. Among them, proanthocyanidins extracted from grape seeds are natural cross-linking agents that stabilize the collagen matrix, which are much less toxic than glutaraldehyde. The bovine tendon and pericardium cross-linked by using the proanthocyanidins show more collagen expressions and depositions, no calcification after transplantation, and mechanical strength and enzymatic resistance comparable to the glutaraldehyde treated biological valves. It is speculated that the phenolic hydroxyl groups in the proanthocyanidins can form stable hydrogen bonds with —OH, —COOH, and ε-amino groups in the collagen in the biological heart valves, thereby cross-linking and fixing them. Therefore, the polyphenol compound can be used in the cross-linking treatment of artificial biological valve materials such as porcine pericardia, bovine pericardia, small intestines, swim bladders, and mesenteries, which can effectively reduce the probability of calcification and degeneration of the biological valves and greatly reduce the biotoxicity of the cross-linking agent.

The α-galactosidase and the cross-linking agent for the bio-based material can be used in combination, so as to effectively reduce the immunogenicity of the biological valve material after being implanted into the human body, and improve the anti-calcification performance of the biological valve material.

Example 1

Example 1 provides a method for preparing a biological valve material derived from a swim bladder of a Silver carp, including steps:

Decellularization treatment of the swim bladder of the Silver carp: In sterile condition, cut the swim bladder out from a Silver carp and rinse it several times with a sterile PBS solution; preserve the fresh swim bladder in a PBS solution containing penicillin and streptomycin, and store in an ice pack for later use. In the PBS solution containing penicillin and streptomycin, the concentration of penicillin is 100 U/mL, and the concentration of streptomycin is 0.1 mg/mL. Then, the swim bladder of the Silver carp is decellularized, including the steps: place the swim bladder in a 1% SDS solution for 6 hours at room temperature, transfer it to a 1% Triton X-100 for 30 minutes at room temperature, and then immerse and rinse it in a PBS solution for 48 hours. After that, place the swim bladder in a solution containing 0.2 mg/mL DNase and 20 mg/mL RNase and shake overnight to digest and obtain the decellularized swim bladder. Then, rinse the decellularized swim bladder several times with a sterile PBS solution, and then store in a sterile PBS solution for later use.

Cross-linking of the swim bladder: Immerse the decellularized swim bladder in a 0.625% glutaraldehyde solution (pH value is 7.4) for 12 hours, and rinse it several times with a sterile PBS solution to obtain a swim bladder derived biological valve material. Then, store the swim bladder derived biological valve material in a sterile PBS solution for later use.

Example 2

Example 2 provides a method for preparing a biological valve material derived from a swim bladder of a Grass carp. The preparation method of the Grass carp derived biological valve material is basically the same as that in Example 1, except that the swim bladder of the Silver carp in Example 1 is replaced with the swim bladder of the Grass carp.

Comparative Example 1

Comparative Example 1 provides a method for preparing a biological valve material derived from a swim bladder of a Silver carp. The preparation method of the Silver carp derived biological valve material is basically the same as that in Example 1, except that the swim bladder is not cross-linked.

Comparative Example 2

Comparative Example 2 provides a method for preparing a biological valve material derived from a bovine pericardium. The preparation method of the bovine pericardium derived biological valve material is basically the same as that in Example 1, except that the swim bladder of the Silver carp of Example 1 is replaced with the bovine pericardium.

Figure 2:
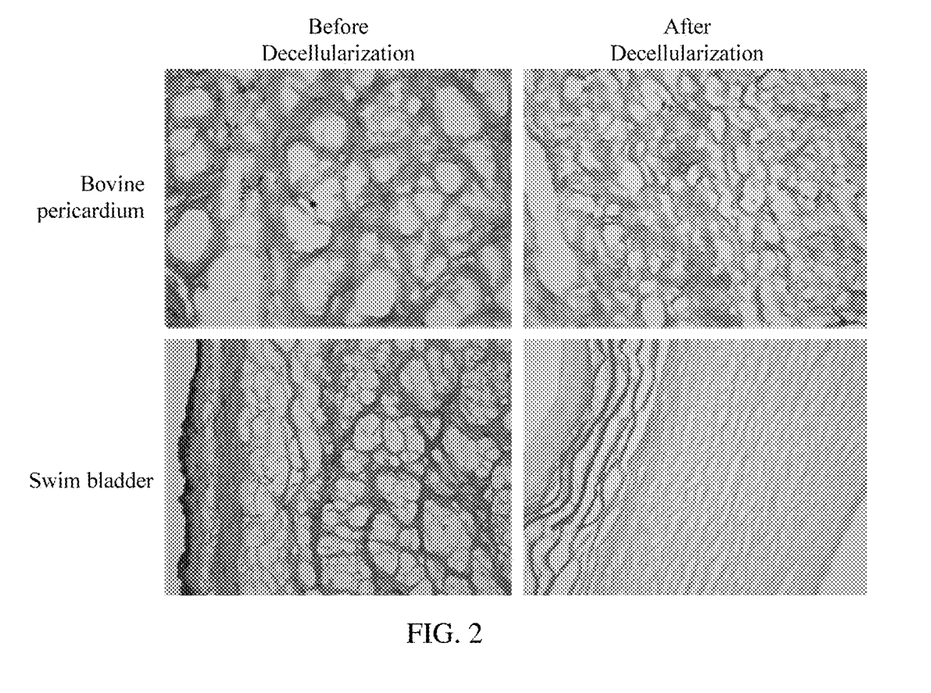
FIG. 2 is a comparison diagram showing decellularization results of biological valve materials in Example 1 and Comparative Example 2 of the present application.

The structures of the biological valve materials of Example 1 and Comparative Example 2 are shown in FIG. 2.

Experimental Example 1: Mechanical Property Test of the Biological Valve Material Derived from the Swim Bladder The biological valve materials of Example 1 (swim bladder, cross-linked), Comparative Example 1 (swim bladder, not cross-linked), and Comparative Example 2 (bovine pericardium, cross-linked) are cut into strips along the collagen fiber direction (y-axis) with a width of about 10 mm and a length of about 25 mm. Each group having three samples is tested for maximum tensile strength and deformation by the Instron material mechanics testing machine at a tensile rate of 5 mm/min, the elastic modulus is the maximum slope of the tensile stress-strain curve.

Figure 3:
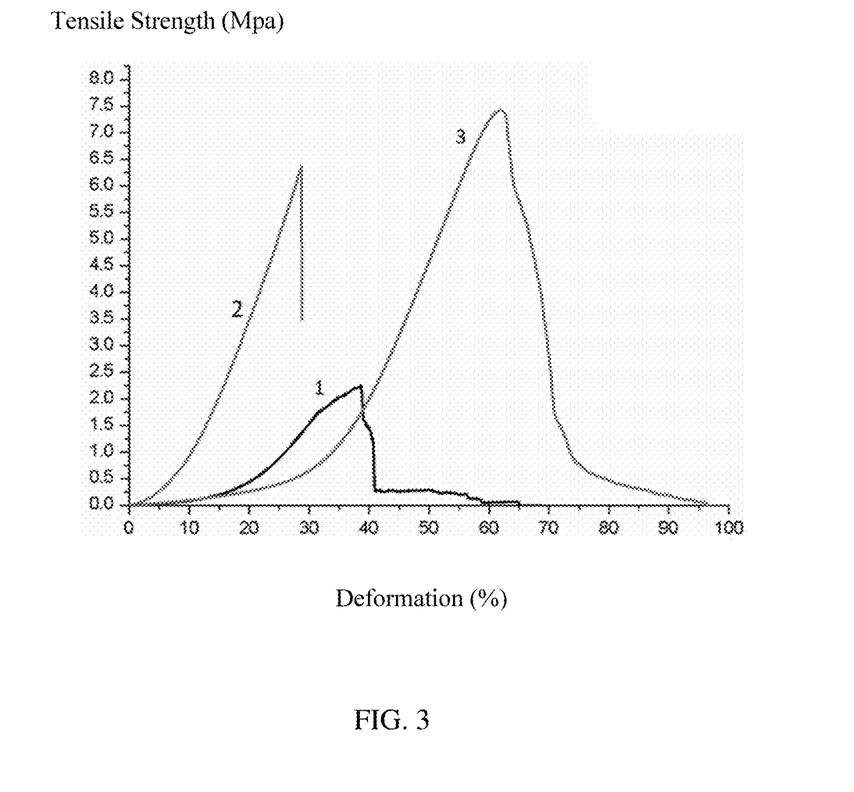
FIG. 3 is a comparison diagram showing the mechanical property curves of the biological valve materials in Comparative Example 1, Example 1, and Comparative Example 2, wherein the curve 1 refers to Comparative Example 1, the curve 2 refers to Example 1, the curve 3 refers to Comparative Example 2.

Referring to FIG. 3, the curve 1 is the mechanical property curve of the swim bladder derived biological valve material without the cross-linking (Comparative Example 1), the curve 2 is the mechanical property curve of the swim bladder derived biological valve material with the cross-linking (Example 1), and the curve 3 is the mechanical property curve of the bovine pericardium derived biological valve material in the control group (Comparative Example 2).

The results reveal that the mechanical property of the swim bladder derived biological valve material with the cross-linking is not significantly different from that of the bovine pericardium derived biological valve material.

Experimental Example 2: Evaluation of Anti-Calcification Performance of the Biological Valve Material Derived from the Swim Bladder After the cross-linking treatment, the swim bladder derived biological valve material (Example 1) and the bovine pericardium derived biological valve material in the control group (Comparative Example 2) are cut into 1 cm×1 cm samples. A 10% chloral hydrate solution is injected into the abdominal cavity of a rat at 0.33 mL/100 g to anesthetize the rat with the back shaved and routinely disinfected with iodine and ethanol. One swim bladder derived biological valve material sample is implanted subcutaneously on the right back and one bovine pericardium derived biological valve material sample is implanted subcutaneously on the left back of the rat. The skin incision is sutured. The implanted samples are taken out after 4 weeks from the animal. The calcium content is determined by tissue staining and atomic absorption spectrometry.

Figure 4:
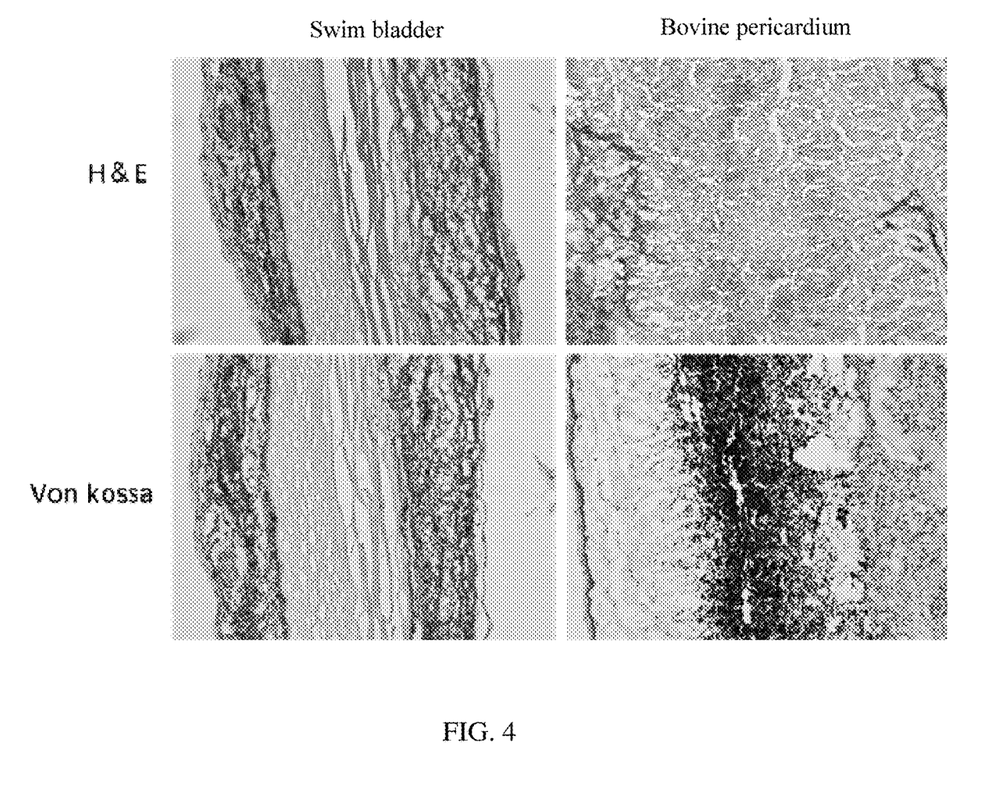
FIG. 4 is a comparison diagram showing anti-calcification performances of the biological valve materials in the rat subcutaneous implant model of Example 1 and Comparative Example 2 of the present application.

Referring to FIG. 4, the analyzing results of the biological valves in the rat subcutaneous implant model show that the anti-calcification performance of the swim bladder derived biological valve material is significantly better than that of the bovine pericardial biological valve material.

The results of Experimental Example 1 and Experimental Example 2 show that, the mechanical properties of the swim bladder derived biological valve material provided in the embodiments of the application are substantially equivalent to that of the bovine pericardial material, but the anti-calcification performance is far superior. The swim bladder derived biological valve material of the present application avoids the defect of insufficient lifetime of the bovine pericardial material, solves the problems such as poor durability and easy calcification of the bovine pericardial material.

Example 3

Example 3 provides a polyphenol cross-linking agent. The polyphenol cross-linking agent is prepared by dissolving curcumin in an ethanol solution and then diluting with a PBS phosphate buffer solution. The specific preparation method includes the following steps:

Dissolve 0.8 mg of curcumin in 2 mL of absolute ethanol, and dilute with 200 mL of PBS phosphate buffer solution to prepare a 0.004 mg/mL curcumin solution, and adjust the pH value of the solution to 7.4.

The formula of the PBS phosphate buffer solution (1 L) is as follows: 8 g sodium chloride (NaCl), 1.42 g disodium hydrogen phosphate ($Na_2HPO_4$), 0.27 g potassium dihydrogen phosphate ($KH_2PO_4$), and 0.2 g potassium chloride (KCl).

Example 4

Example 4 provides a polyphenol cross-linking agent. The polyphenol cross-linking agent is prepared by dissolving resveratrol in an ethanol solution and then diluting with a PBS phosphate buffer solution. The specific preparation method includes the following step:

Dissolve 100 mg of resveratrol powder in 4 mL of absolute ethanol, and dilute with 6 mL of PBS phosphate buffer solution to prepare a 10.0 mg/mL resveratrol solution, and adjust the pH value of the solution to 7.4.

The formula of the PBS phosphate buffer solution (1 L) is as follows: 8 g sodium chloride (NaCl), 1.42 g disodium hydrogen phosphate ($Na_2HPO_4$), 0.27 g potassium dihydrogen phosphate ($KH_2PO_4$), and 0.2 g potassium chloride (KCl).

Example 5

Example 5 provides a polyphenol cross-linking agent. The polyphenol cross-linking agent is prepared by dissolving aloe emodin in an ethanol solution and then diluting with a PBS phosphate buffer solution. The specific preparation method includes the following steps:

Dissolve 3 mg of aloe emodin in 20 mL of absolute ethanol, and dilute with 80 mL of PBS phosphate buffer solution to prepare a 0.03 mg/mL aloe emodin solution, and adjust the pH value of the solution to 7.4.

The formula of the PBS phosphate buffer solution (1 L) is as follows: 8 g sodium chloride (NaCl), 1.42 g disodium hydrogen phosphate ($Na_2HPO_4$), 0.27 g potassium dihydrogen phosphate ($KH_2PO_4$), and 0.2 g potassium chloride (KCl).

Example 6

Example 6 provides a method for preparing a fully decellularized bovine pericardium derived biological valve material, using the curcumin solution prepared in Example 3, and including the steps:

(1) A heart of a freshly slaughtered bovine is taken out and stored in a 4° C. storage and transportation solution; the storage and transportation solution is a PBS solution containing penicillin and streptomycin, wherein the concentration of penicillin is 100 U/mL and the concentration of streptomycin is 0.1 mg/mL.

Within 4 hours, in a sterile environment, the bovine pericardium is cut from the fresh bovine heart, has the surface fat removed, and then rinsed with deionized water and a PBS solution several times.

(2) Pericardial cells are removed from the treated bovine pericardium by applying 1% SDS at room temperature for 6 hours. The shaking speed of the pericardial cell removal process is 100 rpm. Then, the pericardium is rinsed several times with a PBS solution to remove residual SDS solution, and then treated with 1% Triton X-100 for 2.0 hours at room temperature.

(3) The treated bovine pericardium after (2) is rinsed with a PBS solution at 4° C. for 10 days to remove residual solution and cell debris. Then, the pericardium is shaken in 2 U/mL DNase at 37° C. for 15 hours at a constant speed of 120 rpm to remove the nucleus.

(4) The treated bovine pericardium after (3) is shaken in a PBS solution at 120 rpm for 12 hours to completely remove the pericardial cell residues, debris, and free proteins and nucleic acids to obtain the completely decellularized bovine pericardial material. The material is stored in a sterile PBS solution at 4° C. for later use.

The fully decellularized bovine pericardium material is immersed in the curcumin solution prepared in Example 3 for cross-linking. The cross-linking temperature is 25° C., and the shaking speed of the cross-linking is 100 rpm.

After 24 hours of cross-linking, the material is thoroughly washed with a PBS solution. The washed bovine pericardium material is immersed in a PBS solution for 2 days of post-processing to obtain a bovine pericardium derived biological valve material, which is then stored in a PBS solution at 4° C. for later use.

Example 7

Example 7 provides a method for preparing a fully decellularized bovine pericardium derived biological valve material. Example 7 is basically the same as Example 6, except that the cross-linking agent is the resveratrol solution prepared in Example 4, and the cross-linking time is 48 hours.

Example 8

Example 8 provides a method for preparing a fully decellularized bovine pericardium derived biological valve material. Example 8 is basically the same as Example 6, except that the cross-linking agent is the aloe emodin solution prepared in Example 5, and the cross-linking time is 36 hours.

Comparative Example 3

Comparative Example 3 provides a method for preparing a fully decellularized bovine pericardium derived biological valve material. Comparative Example 3 is basically the same as Example 6, except that the cross-linking is not performed.

Comparative Example 4

Comparative Example 4 provides a method for preparing a fully decellularized bovine pericardium derived biological valve material. Comparative Example 4 is basically the same as Example 6, except that the cross-linking agent is a glutaraldehyde solution.

Experimental Example 3: Histological Staining

The bovine pericardium derived biological valve material prepared in Example 6 is treated with 4% paraformaldehyde for 6 hours, washed several times with a PBS solution, and dehydrated in 30% (w/v) sucrose until the sample sank to the bottom. Then, the sample is embedded in the optimal cutting temperature compound (OCT), frozen sectioned at −20° C. into 6 μm in thickness, and H&E stained for histological analysis of decellularization and extracellular matrix collagen arrangement.

Figure 5:
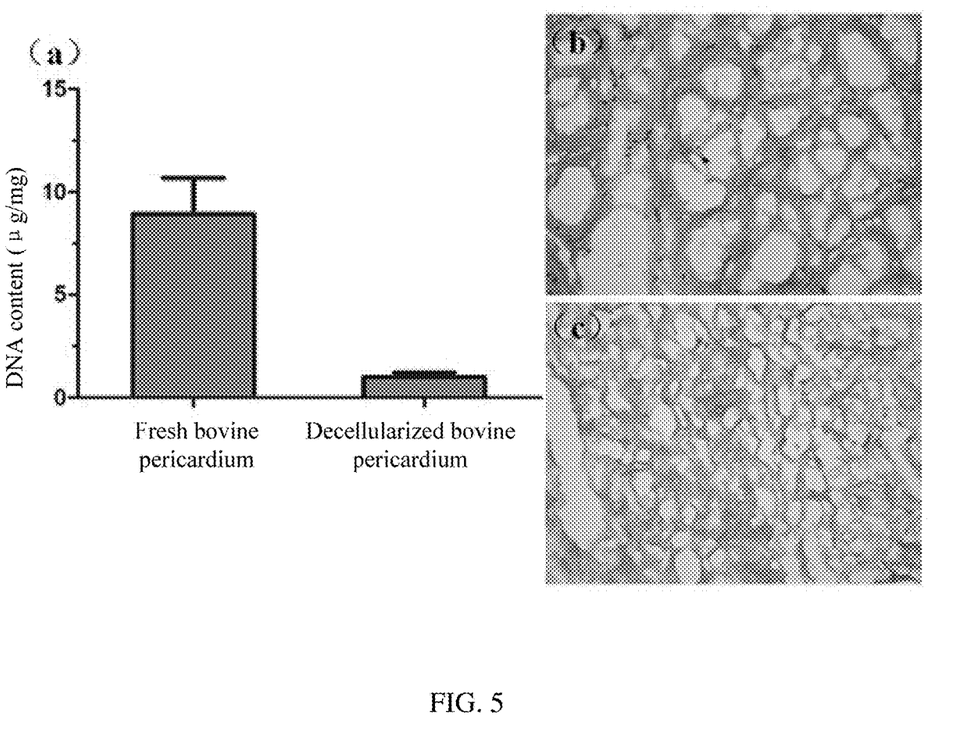
FIG. 5 is an analysis diagram of a decellularized bovine pericardial biological valve material according to an embodiment of the present application, wherein (a) shows the DNA content of the decellularized bovine pericardial biological valve material, (b) is the decellularized state after H&E staining, and (c) is the extracellular matrix collagen arrangement.

Referring to FIG. 5, the bovine pericardial biological valve material after the decellularization has almost no nucleus, indicating a thorough decellularization, which greatly avoids immunogenicity. The extracellular matrix collagen fibers of the bovine pericardial biological valve material after the decellularization are continuous and complete, in reticulated or wavy shapes.

Experimental Example 4: Mechanical Property Test

The non-crosslinked (Comparative Example 3), polyphenol crosslinked (Examples 6-8) and glutaraldehyde crosslinked (Comparative Example 4) bovine pericardium derived biological valve materials are previously stored in a PBS phosphate solution. The mechanical properties of the materials in wet state are tested as follows. The bovine pericardium derived biological valve material is cut into samples (n=3) with a 10 mm*30 mm size along the direction of collagen fibers. The tensile speed is 10 mm/min (model 3345, Norwood, MA). The stress-strain curves are analyzed to obtain the maximum tensile strength, the elastic modulus, and the elongation at break.

Figure 6:
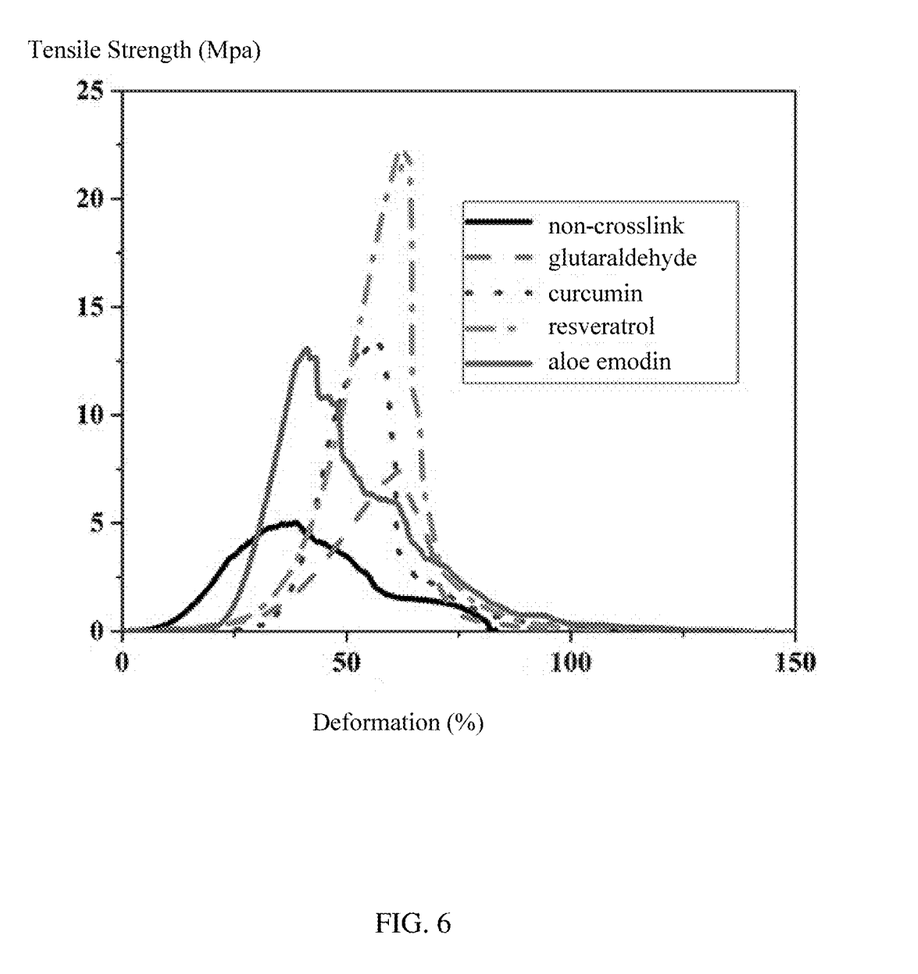
FIG. 6 is a comparison diagram showing mechanical property curves of biological valve materials of Comparative Example 3, Examples 6-8, and Comparative Example 4 of the present application.

The results of the examples and comparative examples are shown in FIG. 6 and Table 1.

TABLE 1

| Results of maximum tensile strength, elastic modulus, and elongation at break | | | | | |
|---|---|---|---|---|---|
| Mechanical strength | Non-crosslinking | Glutaraldehyde | Curcumin | Resveratrol | Aloe emodin |
| Maximum tensile strength (MPa) | 6.01 ± 1.27 | 8.35 ± 1.31 | 12.30 ± 1.72 | 20.61 ± 4.11 | 12.85 ± 2.01 |
| Elastic modulus (MPa) | 20.74 ± 6.69 | 34.42 ± 8.15 | 78.49 ± 17.28 | 87.89 ± 12.66 | 85.73 ± 25.78 |
| Elongation at break (%) | 47.66 ± 7.75 | 56.68 ± 7.27 | 53.67 ± 4.98 | 63.80 ± 1.40 | 38.61 ± 7.19 |

The results shown in FIG. 6 and Table 1 reveal that the 0.004 mg/mL curcumin cross-linked bovine pericardial biological valve material has the maximum tensile strength of 12.30±1.72 MPa, the elastic modulus of 78.49±6.34 MPa, and the elongation at break of 53.67±4.98%; the 10.0 mg/mL resveratrol cross-linked bovine pericardial biological valve material has the maximum tensile strength of 20.61±4.11 MPa, the elastic modulus of 87.89±12.66 MPa, and the elongation at break of 63.80±1.40%; the 0.03 mg/mL aloe emodin cross-linked bovine pericardial biological valve material has the maximum tensile strength of 12.85±2.01 MPa, the elastic modulus of 85.73±25.78 MPa, and the elongation at break of 38.68±1.40%; and the 6.25 mg/mL glutaraldehyde cross-linked bovine pericardial biological valve material has the maximum tensile strength of 8.35±1.31 MPa, the elastic modulus of 34.42±8.15 MPa, and the elongation at break of 56.68±7.27%, which shows that the mechanical properties of the polyphenol cross-linked bovine pericardial biological valve materials are better than those of the glutaraldehyde cross-linked biological valve material.

Experimental Example 5: Evaluation of Calcification of Biological Valve Materials in Subcutaneous Implantation Model The experimental animals are Wistar male young rats in weight of about 50 g. The non-crosslinked (Comparative Example 3), polyphenol crosslinked (Examples 6-8), and glutaraldehyde crosslinked (Comparative Example 4) bovine pericardium derived biological valve materials are cut into 1 cm×1 cm samples. A 10% chloral hydrate solution is injected into the abdominal cavities of the rats at 0.33 mL/100 g to anesthetize the rats with the backs shaved and routinely disinfected with iodine and ethanol. The experimental and comparative bovine pericardium derived biological valve material samples are implanted subcutaneously on the right and left sides of the rat backs. The skin incisions are sutured. The implanted samples are taken out after 2 weeks from the rats which are euthanized.

Figure 7:
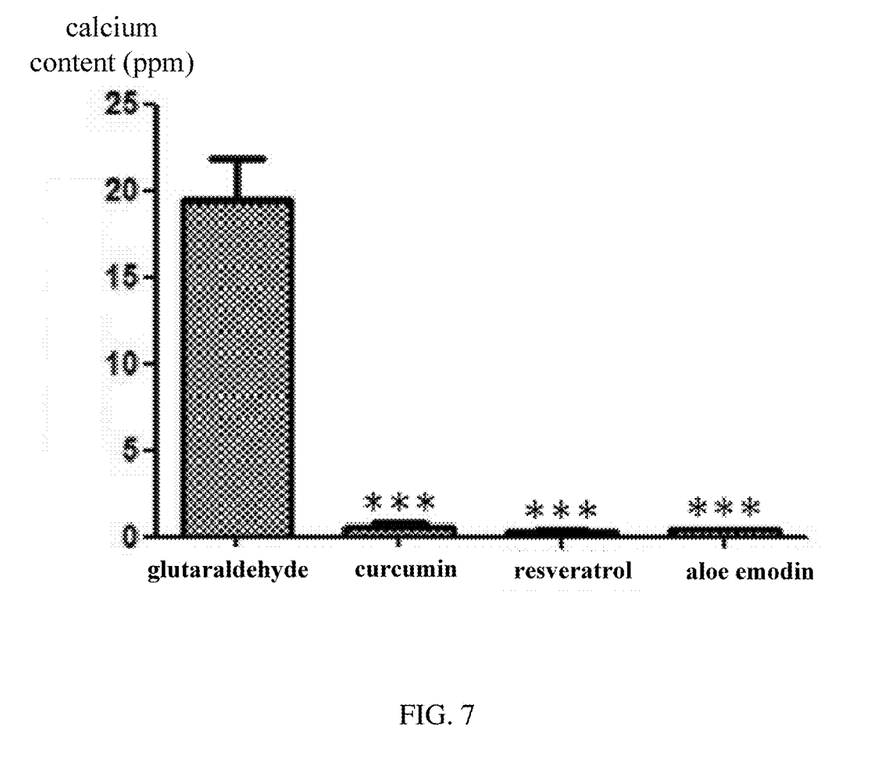
FIG. 7 is a comparison diagram of the calcium content of the biological valve materials of Examples 6-8 and Comparative Example 4 after subcutaneous implantation for 2 weeks.

(1) Determination of calcium content in the tissue by atomic absorption spectrometry: The non-crosslinked, polyphenol crosslinked, glutaraldehyde crosslinked bovine pericardial biological valve materials are accurately weighed after drying at 80° C. for 48 hours, treated with concentrated nitric acid and hydrogen peroxide, and digested in microwave after hydrogen treatment, and diluted to volume with ultrapure water. The content of calcium is measured by atomic absorption spectrophotometry and the results are shown in FIG. 7. The concentrations of calcium standard solutions are 0.0 μg/mL, 0.5 μg/mL, 1.0 μg/mL, 4.0 μg/mL, 8.0 μg/mL.

(2) Qualitative observation of calcification by histological staining: H&E and Von Kossa staining directly reflect the histological changes of the samples and the distribution of the local calcification points. The results are shown in FIG. 8 and FIG. 9.

Referring to FIG. 7, after the two week subcutaneous implantation of the decellularized bovine pericardial biological valve materials cross-linked by the natural polyphenol compounds and the conventional glutaraldehyde cross-linking agent, the test results shows that the calcification rates of the decellularized bovine pericardial biological valve materials cross-linked by the natural polyphenol compounds are very low, indicating the excellent anticalcification properties of the polyphenols used in the examples of the present application as the cross-linking agents for biological valve materials. *** indicates p<0.001, meaning significant differences between groups.

Figure 8:
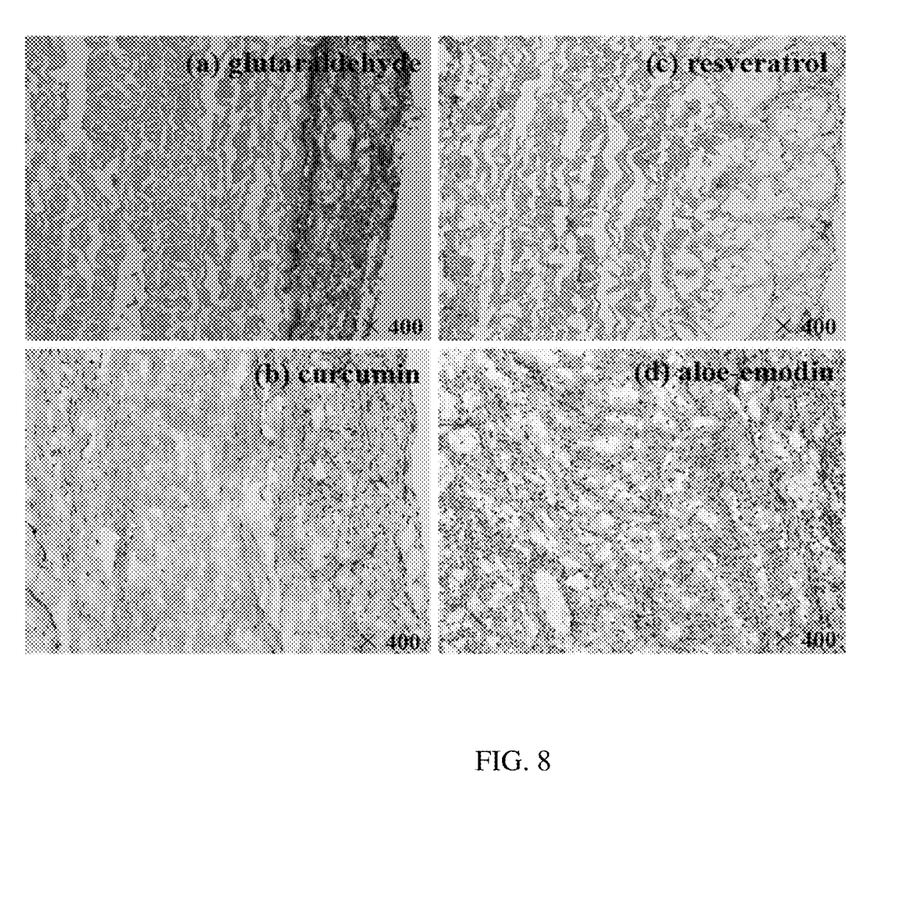
FIG. 8 is a comparison diagram of H&E staining of the biological valve materials of Examples 6-8 and Comparative Example 4 after subcutaneous implantation for 2 weeks.
Figure 9:
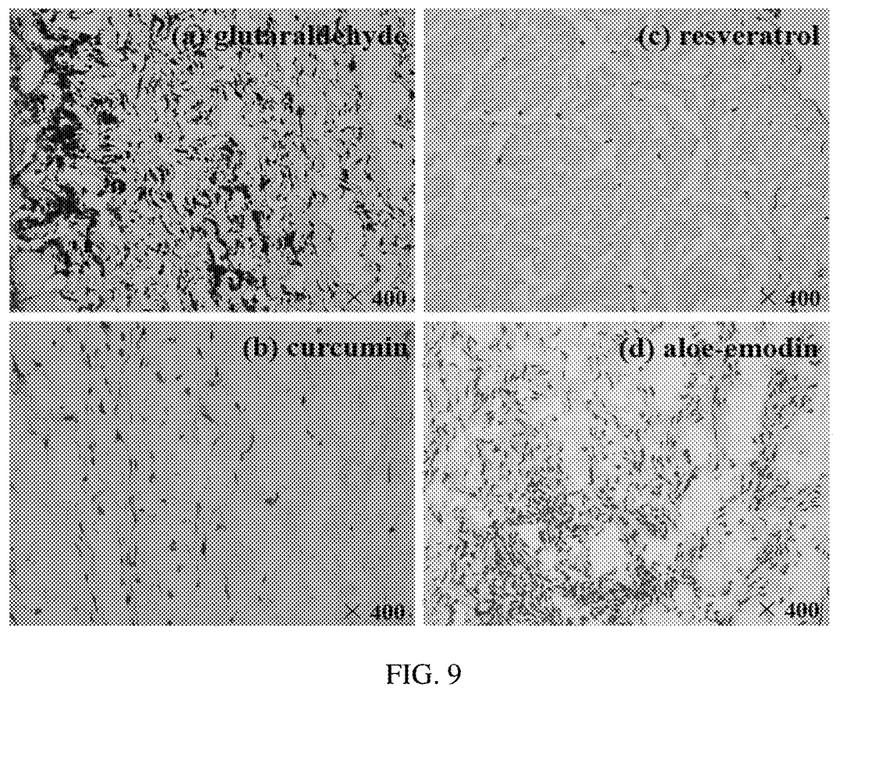
FIG. 9 is a comparison diagram of Von Kossa staining of the biological valve materials of Examples 6-8 and Comparative Example 4 after subcutaneous implantation for 2 weeks.

Referring to FIG. 8 and FIG. 9, after the two week subcutaneous implantation, the H&E staining results show that the cell infiltrations in the curcumin, resveratrol, and aloe emodin cross-linked materials are much better than that of the glutaraldehyde cross-linked material, and the degree of inflammation is much lower than that of the glutaraldehyde cross-linked material. The Von Kossa staining results show almost no calcium nodules in the curcumin, resveratrol, and aloe emodin cross-linked bovine pericardial biological valve materials, while a large amount of calcium deposition in the glutaraldehyde cross-linked material indicates a severe calcification. The results reveal that the anti-calcification performance of the polyphenol cross-linked bovine pericardium is much better than that of the glutaraldehyde cross-linked bovine pericardium. The excellent mechanical properties and anti-calcification performance as a whole indicate a good application prospect of the polyphenol cross-linking agent in the biological valves.

The experimental results of Examples 1-8 and Comparative Examples 1-4 show that the swim bladder derived biological valve material has better mechanical properties and anti-calcification performance than the conventional biological valve materials. In addition, the polyphenol cross-linking agent can further improve the mechanical properties and anti-calcification performance of the biological valve.

The technical features of the above-described embodiments can be arbitrarily combined. In order to make the description simple, not all possible combinations of the technical features in the above embodiments are described. However, as long as there is no contradiction in the combination of these technical features, the combinations should be in the scope of the present disclosure.

What described above are only several implementations of the present disclosure, and these embodiments are specific and detailed, but not intended to limit the scope of the present disclosure. It should be understood by the skilled in the art that various modifications and improvements can be made without departing from the conception of the present disclosure, and all fall within the protection scope of the present disclosure. Therefore, the patent protection scope of the present disclosure is defined by the appended claims.

What is claimed is:

1. A method for preparing a biological valve material, comprising:
   decellularizing a raw swim bladder; and
   cross-linking the decellularized swim bladder with a cross-linking agent to obtain a swim bladder derived biological valve material;
   wherein the cross-linking agent comprises a cross-linking compound, the cross-linking compound comprises glutaraldehyde, and a mass percentage of glutaraldehyde in the cross-linking agent is in a range from 0.5% to 1%.

2. The method of claim 1, wherein the raw swim bladder is a fresh swim bladder preserved in a buffer solution containing penicillin and streptomycin.

3. The method of claim 2, wherein in the buffer solution, a concentration of penicillin is 50 U/mL to 150 U/mL, and a concentration of streptomycin is 0.05 mg/mL to 0.5 mg/mL.

4. The method of claim 1, wherein the step of decellularizing comprises:
   treating the raw swim bladder with a surfactant solution;
   soaking the raw swim bladder after the surfactant treatment in a buffer solution for 1 day to 20 days; and
   treating the raw swim bladder, after the soaking in the buffer solution, in a solution containing deoxyribonuclease and ribonuclease.

5. The method of claim 4, wherein the step of treating the raw swim bladder with the surfactant solution comprises:
   treating the raw swim bladder in an anionic surfactant solution with a mass percentage of 0.05% to 2% at room temperature for 6 hours to 24 hours; and
   treating the raw swim bladder, after the anionic surfactant treatment, in a non-ionic surfactant solution with a mass percentage of 0.05% to 2% at room temperature for 30 minutes to 120 minutes.

6. The method of claim 4, wherein in the solution containing deoxyribonuclease and ribonuclease, the concentration of deoxyribonuclease is 0.1 mg/mL to 0.3 mg/mL, and the concentration of the ribonuclease is 15 mg/mL to 20 mg/mL.

7. The method of claim 1, wherein before cross-linking the swim bladder, the method further comprises irradiating the swim bladder after the decellularization treatment with cobalt-60 for 1 hour to 72 hours.

8. The method of claim 1, wherein the step of cross-linking the decellularized swim bladder with the cross-linking agent comprises: immersing the decellularized swim bladder in the cross-linking agent.

9. The method of claim 1, wherein the temperature of the cross-linking is 10° C. to 40° C., and the time of the cross-linking is 10 minutes to 48 hours.

10. The method of claim 1, wherein the cross-linking compound further comprises a polyphenol compound.

11. The method of claim 1, wherein the cross-linking agent further comprises an organic solvent or an aqueous solution, and the cross-linking compound is dissolved in the organic solvent or the aqueous solution, the organic solvent is selected from the group consisting of ethanol, dimethyl sulfoxide, and a combination thereof, and the aqueous solution is selected from the group consisting of a PBS solution, a D-Hanks solution, and a combination thereof.

12. The method of claim 11, wherein the cross-linking compound comprises a polyphenol compound, and a ratio of a mass of the polyphenol compound to a volume of the organic solvent is 1 mg:(0.1 to 1000.0) mL.

13. The method of claim 1, wherein the cross-linking agent further comprises a buffer solution, and the buffer solution is an aqueous solution.

14. The method of claim 1, wherein the pH value of the cross-linking agent is 5.0 to 9.0.

15. The method of claim 1, before the step of decellularizing, further comprising:
rinsing the raw swim bladder multiple times with a buffer solution, which is a sterile solution.

16. The method of claim 1, wherein the swim bladder is obtained from a fish selected from the group consisting of Silver carp, Grass carp, Amur carp, Yellow croaker, Sturgeon, Scomberomorus, Sciaenidae, and combinations thereof.

17. The method of claim 10, wherein the polyphenol compound is selected from the group consisting of proanthocyanidins, curcumin, resveratrol, puerarin, aloin, aloe emodin, and combinations thereof.

* * * * *